United States Patent [19]

Hoy, Jr.

[11] Plant 4,986

[45] Mar. 1, 1983

[54] SEEDLING ROSE NO. 76-23R

[75] Inventor: Lowell L. Hoy, Jr., Richmond, Ind.

[73] Assignee: Joseph H. Hill Company, Richmond, Ind.

[21] Appl. No.: 300,941

[22] Filed: Sep. 10, 1981

[51] Int. Cl.[3] ..... A01H 5/00

[52] U.S. Cl. ..... Plt./20

[58] Field of Search ..... Plt./20, 28–29

*Primary Examiner*—Robert E. Bagwill

*Attorney, Agent, or Firm*—Chas. W. Rummler

[57] ABSTRACT

A red grandiflora rose for greenhouse culture and the production of cut flowers, this new variety being characterized by its free, vigorous, upright and much branched growth habit with free and abundant continuous production of flowers in greenhouse; a particular distinctiveness of this new variety being its attractive, long pointed bud at cutting stage, its excellent vase life as a cut flower and its abundant production of foliage comprising leaves of relatively large size.

1 Drawing Figure

BACKGROUND OF THE NEW PLANT

This new rose plant originated as a seedling resulting from crossings of unnamed and unpatented seedlings made by me in the Spring of 1974 at Richmond, Ind., with the object of producing a variety with medium sized blooms carried on longer than average stems for a good grandiflora. The flowers appeared in the Fall of 1975 and this particular plant was selected by me because of its more vigorous growth with sturdier, longer stems and more attractive pointed buds than its seed parent, and because of its more profuse and upright growing habits than the habits of its pollen parent. Extensive testing of this new plant through repeated propagations under my direction, by grafting at Richmond, Ind., and by budding at Hamilton City, Calif., has demonstrated that the attractive and distinctive characteristics of this new plant hold true from generation to generation and appear to be firmly fixed.

DESCRIPTION OF THE DRAWING

My new rose plant is illustrated by the accompanying photographic drawing which, in full color, shows a face view of a newly opened flower, buds in two stages of opening, specimens of inside, intermediate and outside petals of the opened bud, specimens of the inside, intermediate and outside petals of the fully opened flower, and specimens of foliage and wood, the color rendition of this drawing being as nearly true as is reasonably possible to obtain by conventional photographic procedures.

DESCRIPTION OF THE NEW VARIETY

The following is a detailed description of my new rose variety based upon observations of plants grown in greenhouse at Richmond, Ind., in April of 1981, the color designations being according to Robert S. Wilson's Horticultural Colour Chart (W) and Koster's Colour Guide (K).

THE PLANT

Origin: Seedling identified as No. 76-23R.

Parentage:

*Seed parent.*—An unnamed seedling.

*Pollen parent.*—An unnamed seedling.

Classification: Grandiflora.

Type: Greenhouse plant for production of cut flowers.

Form: Bush.

Growth: Free and vigorous.

Habit: Upright and much branched.

Canes: Medium in diameter.

Main stems:

*Color.*—Sage Green 000861/1 (W).

*Thorns.*—Several of medium length and hooked downward from a short, narrow base. Color: Pod Green 061/1 tinted with Rhodonite Red 0022/1 (W).

*Prickles.*—Few. Color: Pod Green 061/1 tinted with Rhodonite Red 0022/1 (W).

*Hairs.*—None.

Branches:

*Color.*—Spinach Green 0960/2 (W).

*Thorns.*—Several of medium length, hooked downwardly from a short and narrow base. Color: Lilac, Plate No. 48 (K).

*Prickles.*—Few. Color: Lilac, Plate No. 48 (K).

*Hairs.*—None.

New shoots:

*Color.*—Scheeles Green 860/2 (W) washed with Garnet Lake 828/2 (W).

*Thorns.*—Several of medium length hooked downwardly from very short, narrow base. Color: Magenta Rose 027/1 (W).

*Prickles.*—Few. Color: Magenta Rose 027/1 (W).

*Hairs.*—None.

Foliage:

*Quantity.*—Abundant.

*Form of leaves.*—Odd pinnate. Size: Large.

*Leaflets.*—3, 5 and 7 in number. Shape: Ovoid with acuminate apex, irregularly serrate margin and acute base. Color: Young Leaves: Upper Surface — Scheeles Green 860/2 (W) margined with Garnet Lake 828/2 (W). Under Surface — Scheeles Green 860/3 (W) shaded with Garnet Lake 828/3 (W). Mature Leaves: Upper Surface — Nearest color is Holly Green, Plate No. 82 (K). Under Surface — Cedar Green, Plate No. 80 (K).

*Rachis.*—Medium to heavy in character with hairy upper side and moderately prickly under side.

*Stipules.*—Of medium length and width with moderately long points which turn out at an angle of more than 45° and are recurved toward the stem.

THE BUD

Before calyx breaks:

*Size.*—Medium large.

*Form.*—Long pointed with a conspicuous neck and foliaceous appendages on the bud surface with much cut foliaceous parts extending beyond the tip of the bud for about one-quarter or more of the bud length.

*Color of calyx.*—Scheeles Green 860/2 (W).

As the calyx breaks:

*Outside petal color.*—Cardinal Red 822/2 (W).

As the first petal opens:

*Bud size.*—Medium large.

*Bud form.*—Long pointed.

*Color of petals.*—Outside — Cardinal Red 822/2 (W). Inside — Cardinal Red 822 (W).

Character of opening: The bud opens up well in greenhouse.

Sepals: Permanent, spear-shaped, moderately long and curled.

*Color.*—Inside — Pod Green 061/1 (W) covered with white fuzz. Outside — Lettuce Green 861/1 (W) bordered with Scheeles Green 860/2 (W).

Peduncle:

*Character.*—Strong and erect, of medium length and medium diameter.

*Bark.*—Slightly rough. Color: Lettuce Green 861 (W).

*Thorns.*—None.

*Prickles.*—None.

*Hairs.*—Few. Color: Spinel Red 0023/2 (W).

THE FLOWER

Blooming habit: Free, abundant and continuous, in greenhouse.

Size: Medium, 2½ to 3 inches in diameter when fully opened.

Form: Full and high centered at first with petals tightly rolled outward, becoming open at maturity with petals loosely rolled outward.

Borne: In regular clusters on strong stems of medium length, there being several buds to a stem. Stems may be disbudded for commercial use.

Petalage: Double, with 35 to 40 petals arranged regularly.

*Shape.*—Outside petals — Ovate having mucronate apex usually with one notch although some petals may have no notch. Intermediate petals — Ovate with mucronate apex with one notch although some petals may have none. Inside petals — Obovate with mucronate apex and with one to three notches, some inside petals having none.

Flower color:

A. The following is the color description of a newly opened greenhouse flower observed in the month of April 1981 at Richmond, Ind.:

*Outside, intermediate, and inner petals.*—Outside surface — Cardinal Red 822/2 (W). Inside surface — Straw Yellow 604/2 at the base changing to Cardinal Red 822/1 (W).

B. This description was made from a rose that was open for three days in greenhouse in the month of April 1981:

*Outside, intermediate, and inner petals.*—Outer surface — Cardinal Red 822/2 (W). Inside surface — Straw Yellow 604/2 at the base changing to Cardinal Red 822/1 (W).

General color effect of the open bloom:

*Newly opened flower.*—Cardinal Red 822/2 (W).

*Three days opened flower.*—Cardinal Red 822/1 (W).

Fragrance in greenhouse: Musk.

Persistence: The petals hang on and dry.

Lasting quality: Six to seven days in April for cut flowers kept at living room temperatures.

REPRODUCTIVE ORGANS

Stamens: Many in number, arranged irregularly about the pistils.

*Anthers.*—Of medium size and all open at once. Color: Buttercup Yellow 5/3 (W).

*Pollen.*—Abundant. Color: Indian Yellow 6/2 (W).

*Filaments.*—Of medium length. Color: Rhodonite Red 0022 (W).

Pistils: Of medium number.

*Styles.*—Bunched, moderately thin, uneven and of medium length. Color: Rhodonite Red 0022/3 (W).

*Stigma.*—Color — Buttercup Yellow 5/1 (W).

Ovularies: All encased in calyx.

Hips: None.

Seeds: No seeds have been noted.

This new rose variety is in general similar to "Mary DeVor" (U.S. Plant Pat. No. 2,838). It is similar in stem length; however, the bud and color of the open bloom is brighter throughout the entire year. Also, the new plant is particularly distinguished by its attractive, long pointed bud at cutting stage, its sturdy, upright and vigorous growth habit and prolific production of flowers. This new plant has no special cultural requirements and its foliage does not sunburn in greenhouse.

I claim:

1. A new and distinct variety of rose plant, substantially as herein shown and described, characterized by its abundant and continuous production of flowers, its free and vigorous growth habit and its long pointed bud at cutting stage.

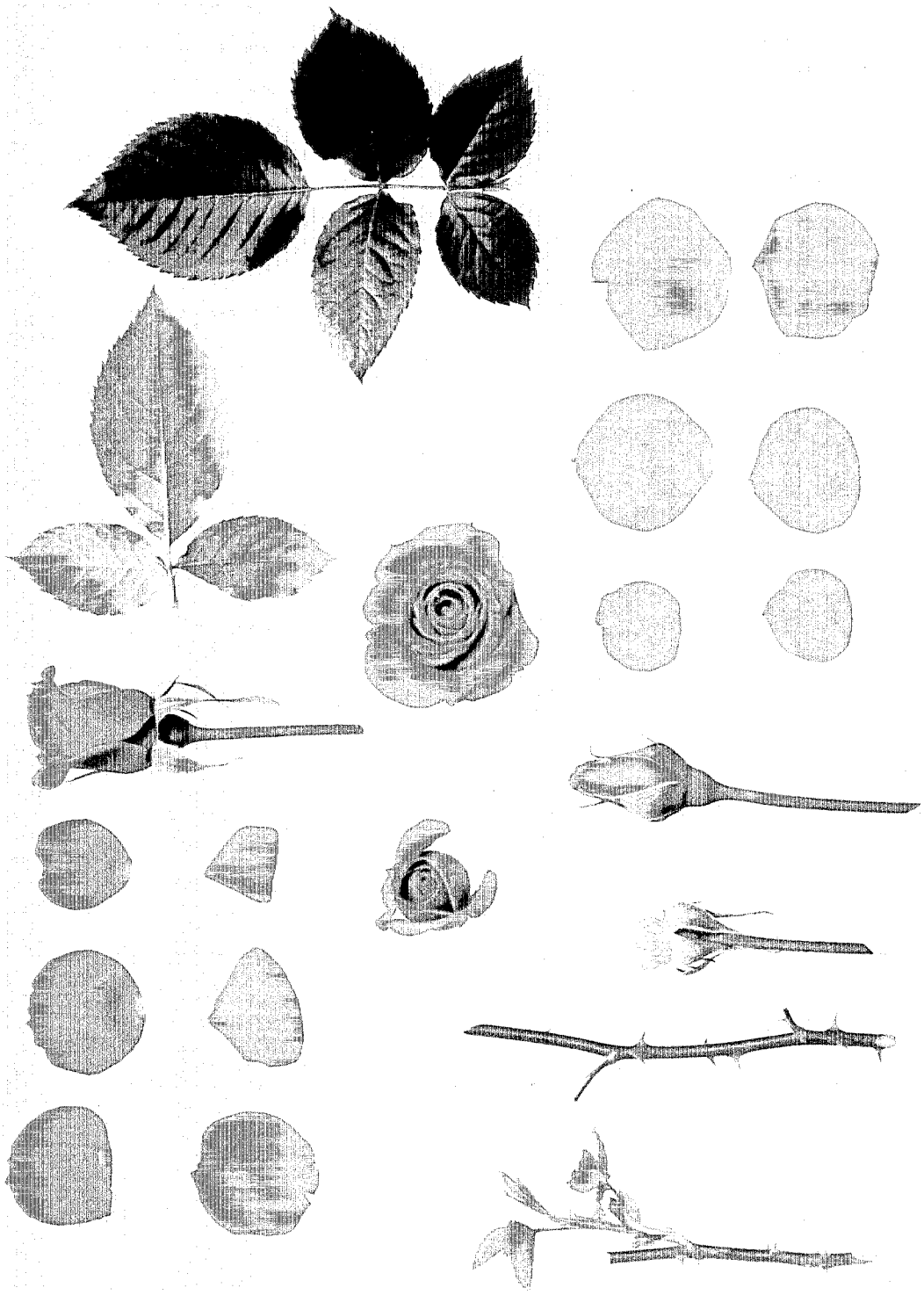

* * * * *